(12) United States Patent
Holland et al.

(10) Patent No.: US 10,546,072 B2
(45) Date of Patent: *Jan. 28, 2020

(54) OBTAINING MICRO- AND MACRO-ROCK PROPERTIES WITH A CALIBRATED ROCK DEFORMATION SIMULATION

(71) Applicants: Marc Holland, The Hague (NL); Tobias Hoeink, Houston, TX (US); Wouter Van Der Zee, Voorburg (NL)

(72) Inventors: Marc Holland, The Hague (NL); Tobias Hoeink, Houston, TX (US); Wouter Van Der Zee, Voorburg (NL)

(73) Assignee: BAKER HUGES, A GE COMPANY, LLC, Houston, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 16/160,453

(22) Filed: Oct. 15, 2018

(65) Prior Publication Data
US 2019/0057168 A1 Feb. 21, 2019

Related U.S. Application Data

(63) Continuation-in-part of application No. 15/082,109, filed on Mar. 28, 2016, now Pat. No. 10,102,311.

(51) Int. Cl.
*G06F 17/50* (2006.01)
*E21B 49/00* (2006.01)
(Continued)

(52) U.S. Cl.
CPC ........ *G06F 17/5004* (2013.01); *E21B 49/003* (2013.01); *E21B 49/081* (2013.01);
(Continued)

(58) Field of Classification Search
CPC combination set(s) only.
See application file for complete search history.

(56) References Cited

U.S. PATENT DOCUMENTS 6,795,773 B2 9/2004 Soliman et al.
9,316,568 B2 4/2016 He et al.
(Continued)

FOREIGN PATENT DOCUMENTS

WO 2014105659 A1 7/2014

OTHER PUBLICATIONS

FY14 Annual Progress Report; Laboratory Directed Research and Development; Mar. 2015; 895 pages.
(Continued)

*Primary Examiner* — Mamadou L Diallo
(74) *Attorney, Agent, or Firm* — Cantor Colburn LLP

(57) ABSTRACT

A method for estimating a property of an earth formation includes: obtaining a sample of rock; scanning the sample to determine internal rock damage; measuring a deformation parameter of the sample; constructing a mathematical model of the sample that replicates the determined and measured internal rock damage distribution; simulating the one or more tests using the mathematical model; obtaining a rock deformation parameter using the one or more simulated tests corresponding to the measured rock deformation parameter; comparing the rock deformation parameter obtained from the one or more simulated tests to the corresponding measured rock deformation parameter; adjusting parameters of the mathematical model based upon the rock parameter obtained from simulation not being within a selected range of the measured rock parameter; and providing the mathematical model as a verified mathematical model based upon the rock parameter obtained from simulation being within a selected range of the measured rock parameter.

19 Claims, 7 Drawing Sheets

(51) Int. Cl.
*E21B 49/08* (2006.01)
*G01V 99/00* (2009.01)
*G01N 33/24* (2006.01)

(52) U.S. Cl.
CPC ......... *G01N 33/241* (2013.01); *G01V 99/005* (2013.01); *G06F 17/5009* (2013.01)

(56) References Cited

U.S. PATENT DOCUMENTS

| | | | |
|---|---|---|---|
| 2006/0131074 | A1 | 6/2006 | Calhoun et al. |
| 2009/0005996 | A1 | 1/2009 | Delorme et al. |
| 2010/0128932 | A1 | 5/2010 | Dvorkin et al. |
| 2010/0135536 | A1 | 6/2010 | Dvorkin et al. |
| 2011/0015907 | A1 | 1/2011 | Crawford et al. |
| 2011/0029293 | A1 | 2/2011 | Petty et al. |
| 2012/0166088 | A1* | 6/2012 | Sallee ............... G01V 1/30 702/11 |
| 2013/0000895 | A1 | 1/2013 | Walters et al. |
| 2013/0006597 | A1 | 1/2013 | Craig |
| 2013/0090902 | A1* | 4/2013 | Yao ............... E21B 43/26 703/2 |
| 2013/0199787 | A1* | 8/2013 | Dale ............... E21B 43/26 166/302 |
| 2013/0211807 | A1 | 8/2013 | Barrett et al. |
| 2013/0308831 | A1 | 11/2013 | Dvorkin et al. |
| 2015/0043787 | A1* | 2/2015 | Fredrich ............ G06F 17/5018 382/109 |
| 2015/0068319 | A1* | 3/2015 | He ............... G01N 3/313 73/838 |
| 2015/0204174 | A1 | 7/2015 | Kresse et al. |
| 2016/0108705 | A1 | 4/2016 | Maxwell et al. |
| 2017/0003263 | A1* | 1/2017 | Huang ............... G01B 21/32 |
| 2017/0052283 | A1 | 2/2017 | Hoeink et al. |
| 2017/0275970 | A1* | 9/2017 | Crawford ............ G01V 99/005 |
| 2017/0277812 | A1 | 9/2017 | Holland et al. |

OTHER PUBLICATIONS

Hoeink, et al.; "Mechanisms-based Fracture Model for Geological Materials"; V3 Apr. 16, 2015; 11pages.

Hoonil, Seoul, et al.; "Shear Load Transfer for Rock-Socketed Drilled Shafts Based on Borehole Roughness and Geological Strength Index (GSI)"; 2008, International Journal of Rock Mechanics & Mining Sciences, vol. 45, pp. 848-861.

International Search Report and the Written Opinion of the International Searching Authority; PCT/US2017/023161; Korean Intellectual Property Office; dated Jun. 15, 2017; 8 pages.

Johan Christian Clausen, et al; "A Simple and Efficient FEN-Implementation of the Modified Mohr-Coulomb Criterion"; 2006; Proceedings of the 19th Nordic Seminar on Computational Mechanics, 7 pages.

Notification of Transmittal of the International Search Report and the Written Opinion of the International Searching Authority, or the Declaration; PCT/US2016/046181; dated Nov. 16, 2016; 11 pages.

Sarris et al.; "The influence of pumping parameters in fluid-driven fractures in weak porous formations"; International Journal for Numerical and Analytical Methods in Geomechanics; 2014; John Wiley & Sons, Ltd.; 21 pages.

Schofield, Jordan; "Optimization of Hydraulic Fracture Stimulation in Field Development"; Sep. 2014; Imperial College London; 38 pages.

Zubelewicz, et al. "Dynamic Behavior of Copper Under Extreme Loading Rates"; J. Phys. IV France 134 (2006); 5 pages.

Zubelewicz, et al.; A Constitutive Model for a Uranium-Niobium Alloy; Journal of Applied Physics 100; (2006); 8 pages.

Zubelewicz, et al.; "A Mechanisms-based model for dynamic behavior and fracture of geomaterials"; Internatiional Journal of Rock Mechanics & Mining Sciences 72 (2014); 6 pages.

Zubelewicz, et al.; "Constitutive Model with Rotating Active Plane and True Stress"; Mar. 1987; Retrieved on Mar. 17, 2010; Retrieved from the internet; URL:http://pubs.asce.org; 19 pages.

Zubelewicz, et al.; "Geometric Interpretation for Huber-von Mises Plasticity"; Apr. 2014; Retrieved from the internet; URL:http://www.researchgate.net/publication/275334193; 8 pages.

Zubelewicz, et al.; "MicroMechanical Study of Ductile and PolyCrystalline Materials";Nov. 1993; Journal of the Mechanics and Physics of Solids; 13 pages.

Zubelewicz, et al.; Fracture Model for Cemented Aggregates; AIP Advances 3, 012119 (2013); 11 pages.

Zubelewicz,Aleksander; "Overall Stress and Strain Rates for Crystalline and Frictional Materials";Int. J. Non-Linear Mecahnics; vol. 25, No. 4;5 pages.

* cited by examiner

US 10,546,072 B2

OBTAINING MICRO- AND MACRO-ROCK PROPERTIES WITH A CALIBRATED ROCK DEFORMATION SIMULATION

CROSS REFERENCE TO RELATED APPLICATIONS

The present application is a continuation-in-part of U.S. patent application Ser. No. 15/082,109 filed Mar. 28, 2016, the entire disclosure of which is incorporated herein by reference.

BACKGROUND

Earth formations may be used for various purposes such as hydrocarbon production, geothermal production, and carbon dioxide sequestration. In order to efficiently employ resources for using an earth formation, it is necessary to know one or more properties or parameters of the earth formation. One example of a property is unconfined compressive strength (UCS). By knowing the UCS of formation rock, a production engineer for example can determine how fast to pump hydrocarbons from a well without producing sand grains. Many types of other actions may also be performed by knowing the properties of formation rock. Therefore, it would be well received in drilling and production industries if techniques were developed to accurately and efficiently estimate properties of earth formations.

BRIEF SUMMARY

Disclosed is a method for estimating a property of an earth formation. The method includes: obtaining a sample of rock from the earth formation; scanning the sample with a volumetric imaging device to obtain a three-dimensional volume representation of the sample; determining internal rock damage of the sample using the three-dimensional volume representation of the sample; performing one or more tests on the sample using a rock test device; measuring a deformation parameter of the sample using a deformation sensor; constructing a mathematical model of the sample that replicates the determined and measured internal rock damage and damage distribution of the sample; simulating the one or more tests using the mathematical model; obtaining a rock deformation parameter using the one or more simulated tests corresponding to the measured rock deformation parameter; comparing the rock deformation parameter obtained from the one or more simulated tests to the corresponding measured rock deformation parameter; adjusting parameters of the mathematical model based upon the rock parameter obtained from simulation not being within a selected range of the measured rock parameter; and providing the mathematical model as a verified mathematical model based upon the rock parameter obtained from simulation being within a selected range of the measured rock parameter; wherein the determining, constructing, obtaining a rock deformation parameter, comparing adjusting, and providing are performed using a processor.

Also disclosed is a system for estimating a property of an earth formation. The system includes: a volumetric imaging device configured to scan a sample of rock form the earth formation to obtain a three-dimensional volume representation of the sample; a rock test device configured to perform one or more tests on the sample; a deformation sensor configured to measure deformation of the sample due to the one or more tests; a memory having computer-readable instructions; and a processor for executing the computer-readable instructions. The computer-readable instructions include: determining internal rock damage of the sample using the three-dimensional volume representation of the sample; constructing a mathematical model of the sample that replicates the determined internal rock damage and damage distribution of the sample; simulating the one or more tests using the mathematical model; obtaining a rock deformation parameter using the one or more simulated tests corresponding to the measured rock deformation parameter; comparing the rock deformation parameter obtained from the one or more simulated tests to the corresponding measured rock deformation parameter; adjusting parameters of the mathematical model based upon the rock parameter obtained from simulation not being with a selected range of the measured rock parameter; and providing the mathematical model as a verified mathematical model based upon the rock parameter obtained from simulation being within a selected range of the measured rock parameter.

BRIEF DESCRIPTION OF THE DRAWINGS

The following descriptions should not be considered limiting in any way. With reference to the accompanying drawings, like elements are numbered alike.

DETAILED DESCRIPTION

Figure 1:
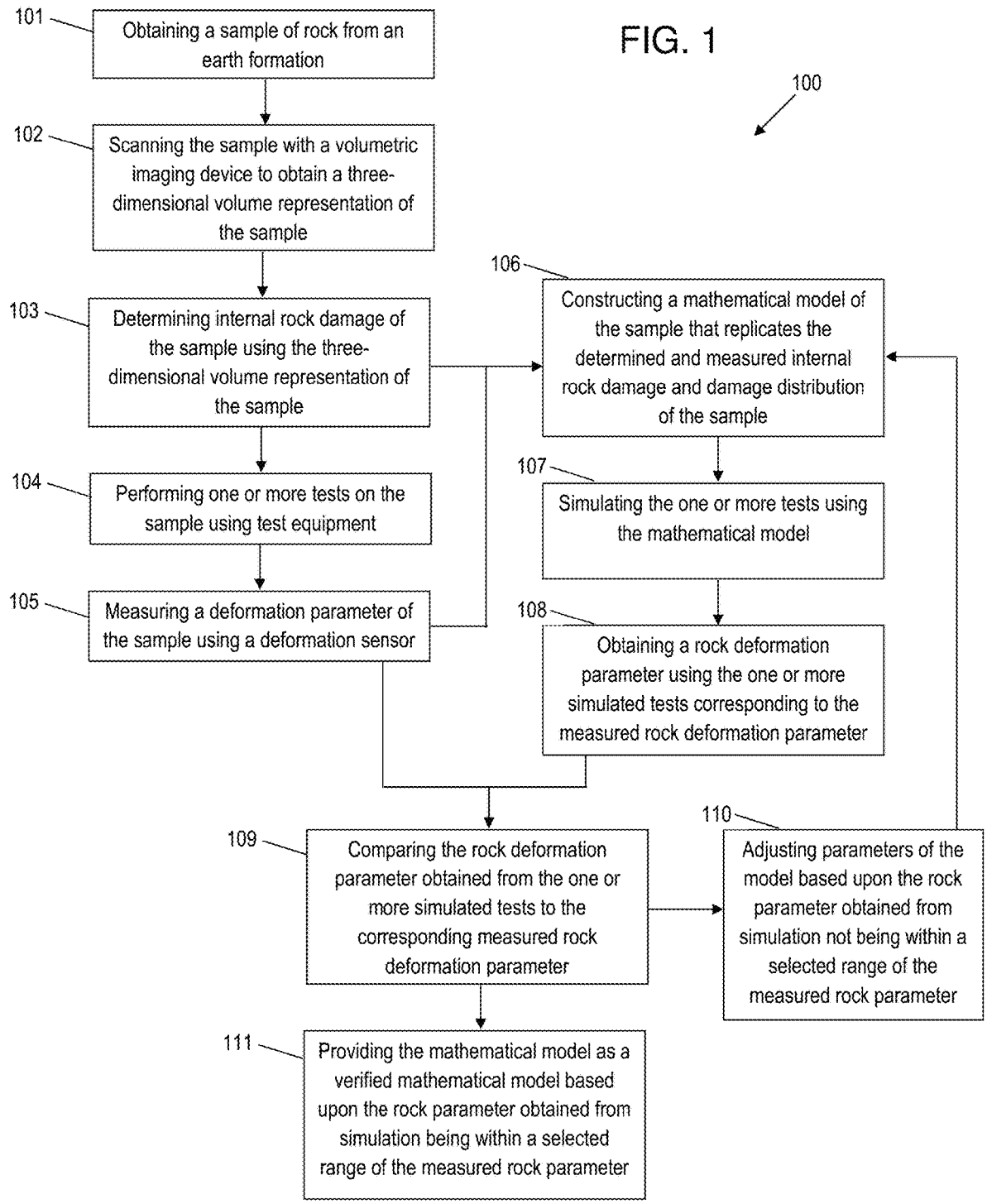
FIG. 1 is a flow chart for a method for estimating a property of rock in an earth formation.

A detailed description of one or more embodiments of the disclosed apparatus and method presented herein by way of exemplification and not limitation with reference to the figures.

Disclosed are methods and apparatus for estimating a property of an earth formation. The methods and apparatus involve simulating formation rock features using a mathematical model of the rock features and calibrating the model using tests of actual samples of the rock. Accurate property values are thus estimated from an accurate rock model. In addition, drilling and/or production actions may be performed on the formation based upon knowledge of the estimated property.

It is noted that testing of rock samples alone may not be sufficient to provide the desired accuracy of estimated property values. The collection of rock parameters from rock tests can be biased due to different reasons. One reason is the rock sampling itself. Common practice involves collecting rock cores e.g. from a wellbore. With this procedure only certain sections of the wellbore may be sampled producing a subset of sample data. From the rock core further subsets are generally created called "plugs". In some cases the plugs are directly collected from the wellbore wall.

On the plugs the rock tests are carried out. The selection of the plugs as samples is based on a variety of decisions which are not discussed in detail here. Important to note however, is that the heterogeneity of the rock column may not be fully represented as the material properties, the coherency or degree of damage (e.g., micro-cracks) may differ from one location to another thus making the plug not fully representative of the earth formation.

The second source of bias may be introduced by the rock tests themselves. Multi-stage rock tests for example are carried out to measure rock stress/strain curves under increasing stress conditions. In these tests the sample is loaded and unloaded repeatedly. In each cycle, deformation is halted before significant inelastic behavior occurs to avoid rock failure that may fully destroy the sample. A destroyed sample would make further measurements impossible. All of these loading cycles however introduce damage to the rock material by crack closing as well as the creation of micro cracks which are linked to the onset of inelastic behavior. Because of this cumulative damage the rock mechanical properties of the sample may change throughout the test and introduce bias.

Apart from these multistage tests, other tests (e.g. unconfined compressive strength measurements) that provide useful information may require the full destruction of the sample during the test procedure, thus, not allowing any other subsequent tests on the same plug.

The main shortcomings testing alone are in summary (a) the lack of fully representing the rock's variability to due to the sampling and (b) the introduction of damage into the sample during the testing up to when its destruction inhibits further rock tests.

To overcome these shortcomings and provide other advantages, the methods and apparatus disclosed herein link the physical rock tests to a simulation of the very same tests or type of tests. The simulation is based on a mathematical material model of the formation rock that has the capability to track and quantify the damage history and damage directionality of the material. This model may be referred to herein as a "micro-crack evolution model." In one or more embodiments, the model is based on a modified Mohr-Coulomb model having a term representing dilatation in an out-of-plane (i.e., out of fracture plane) orientation. U.S. patent application Ser. No. 15/006,281 entitled "Mechanisms-Based Fracture Model For Geomaterials" discloses an example of the mathematical material model and is incorporated by reference in its entirety.

Based on the geometry and property distribution of the physical sample, a digital model (i.e., a mathematical model that is implemented by a processor such as in a computer processing system) is created. The digital model is calibrated against a non-destructive test or a test in which the physical sample is damaged incrementally (e.g. multi-stage test). Model validation is achieved if the parameters of the digital rock model adequately represent the rock deformation parameters of the physical sample. For example, model validation may be achieved if the results of a simulated multi-stage test are the same as the results of an actual multi-stage test for each incremental test.

The verified digital model can then be used to forward model multiple destructive tests. Furthermore, the model is able to separate the micro-properties of the rock matrix as well as the bulk macro-properties of the rock as a result of its internal damage. The model's ability to add a variable degree and distribution of damage to the model allows creation of a rock property catalogue with respect to verifying degrees of damage.

In general, the term "macro-property" relates to a property that is visible to the naked eye, while the term "micro-property" relates to a property that is not readily visible to the naked eye. With respect to each other, macro-properties are physically larger than micro-properties. It can be appreciated that properties may be sample dependent and/or scale dependent (i.e., dependent on physical size of the sample). Hence, micro-properties may be differentiated from macro-properties.

Figure 4:
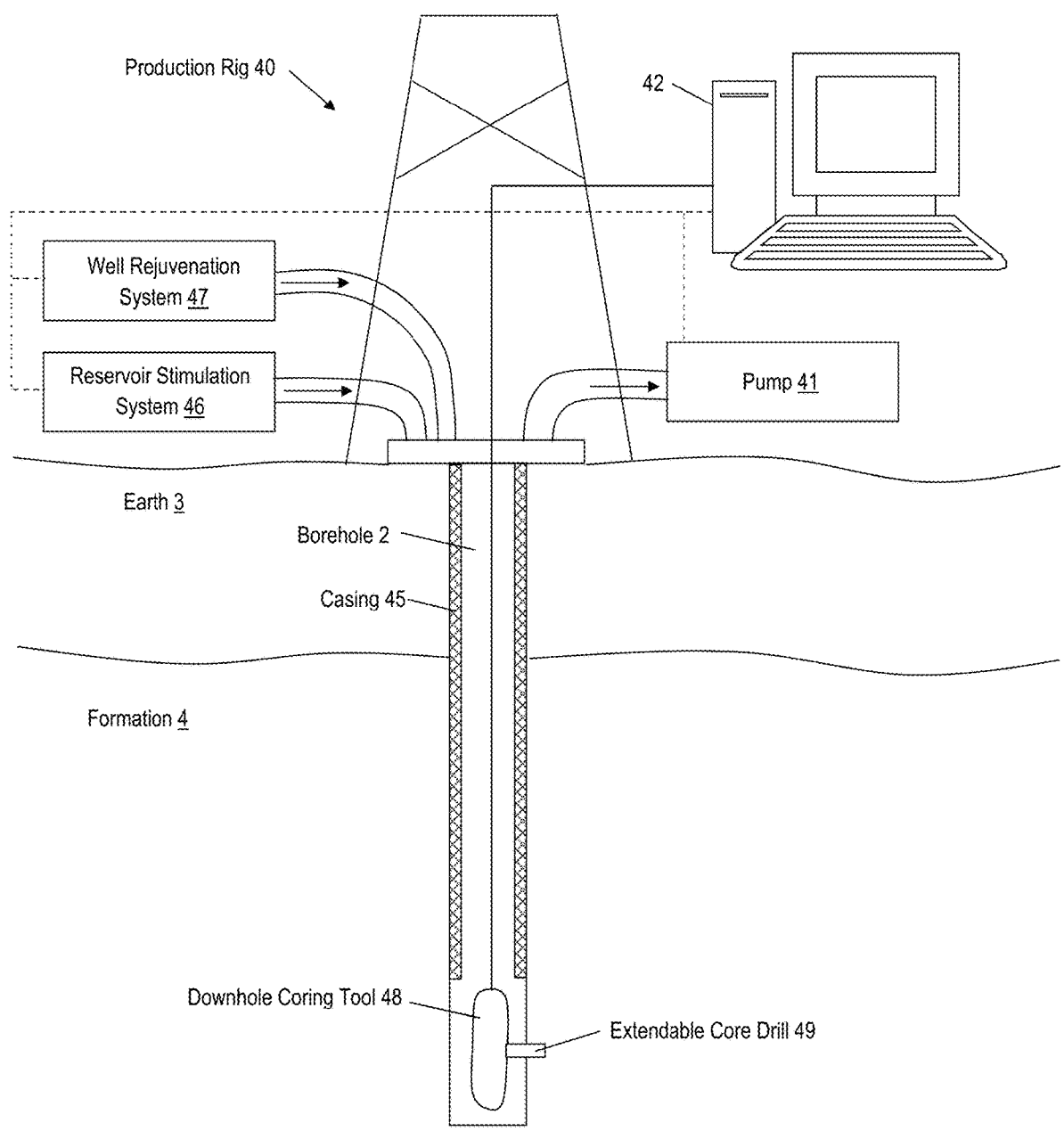
FIG. 4 depicts aspects of production equipment.

FIG. 1 is a flow chart for a method 100 for estimating a property of an earth formation. Block 101 calls for obtaining a sample of rock from the earth formation. The sample may be a sidewall core sample or a core sample of rock being drilled to drill a borehole. In one or more embodiments, a plurality of plugs may be extracted from one core sample. The physical sample may be referred to hereafter as a "plug" but may also represent another form of rock or material sample. The sample may be extracted from a formation using a coring tool such as illustrated in FIG. 4.

Figure 2:
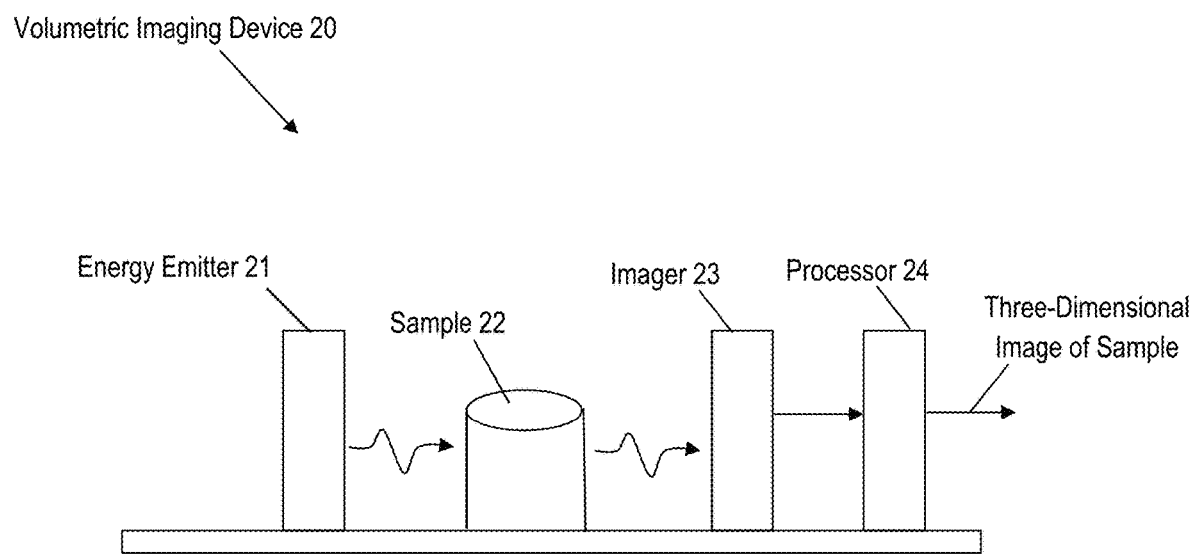
FIG. 2 depicts aspects of a volumetric imaging device for scanning the core sample to determine internal damage to the rock of the core sample.

Block 102 calls for scanning the sample with a volumetric imaging device to obtain a three-dimensional volume representation of the sample. The volumetric characteristics (such as voids, macro-cracks or micro-cracks) of the sample or plug are captured with the volumetric imaging device (e.g. computer tomography). The volumetric imaging device in one or more embodiments captures the radiological density of the plug and stores this information as a volumetric data set. FIG. 2 depicts aspects of one example of a volumetric imaging device 20. The volumetric imaging device 20 includes an energy emitter 21 configured to emit energy into a sample 22 of the rock of the earth formation. The volumetric imaging device or scanner 20 also includes an imager 23 configured to receive energy from the sample 22 due to interaction of the emitted energy with the sample 22 and to provide a three-dimensional image of the sample 22 using the received energy. A processor 24 may process data received from the imager in order to provide the three-dimensional image. Non-limiting embodiments of the energy emitted by the scanner 20 include X-rays. Other types of energy may also be used. In one or more embodiments, the volumetric imaging device is a computed tomography (CT) scanner or micro-CT scanner.

Block 103 calls for determining internal rock damage of the sample with a processor using the three-dimensional volume representation of the sample. The volumetric data is used to derive a representative, statistical and/or discrete data set on matrix material of the sample that quantifies void, micro-crack, and macro-crack distribution in the plug.

Figure 3:
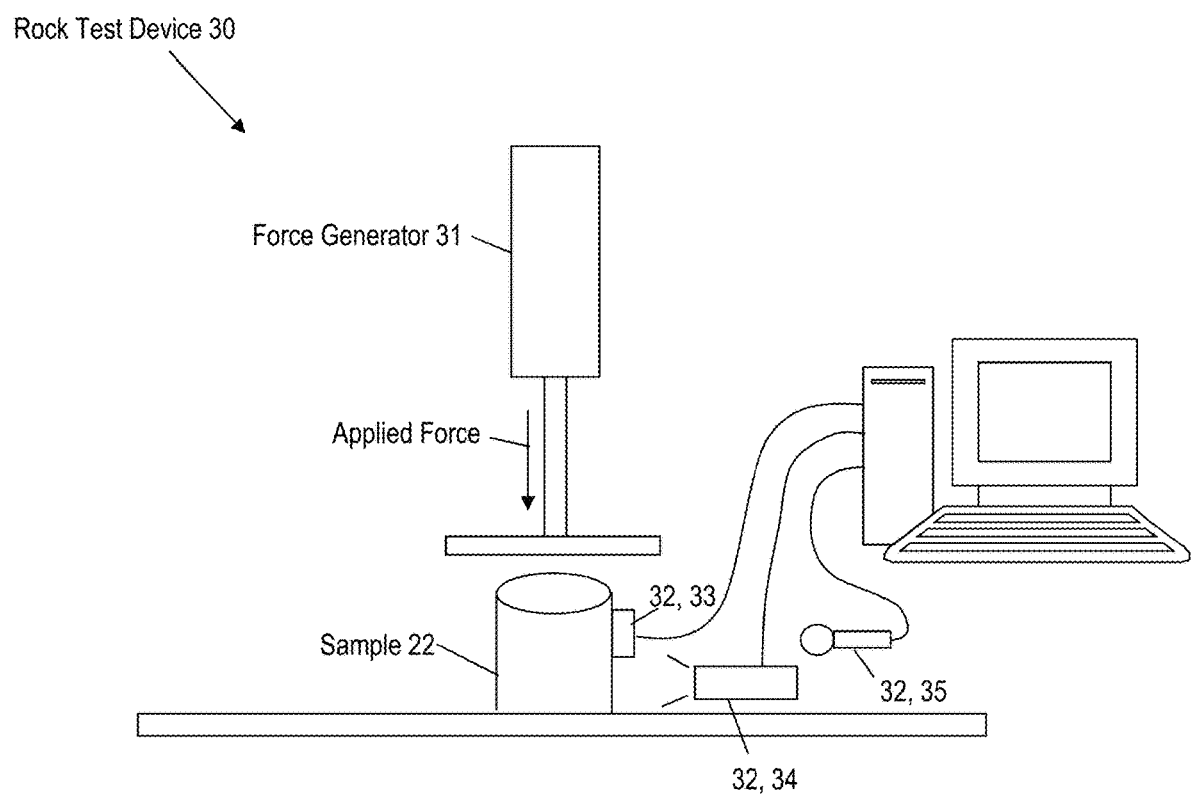
FIG. 3 depicts aspects of a rock test device.

Block 104 calls for performing one or more tests on the sample using a rock test device. The one or more tests may include non-destructive rock tests and/or destructive rock tests that cause rock damage such as a multi-stage rock test. In this block, the plug is subjected to one or more rock tests which may include subjecting the sample to a force in order to capture rock parameters. These may be tests which, ideally, are non-destructive and do not introduce significant damage to the material. The non-destructive and/or destructive tests may include measuring a deformation parameter of the material when a force is applied to the plug. Single-stage rock tests and/or multistage stage rock tests to capture the stress/strain behavior may be carried out next. This complements the rock property catalogue but is expected to introduce damage to the plug. FIG. 3 depicts aspects of a rock test device 30. The rock test device 30 may include a force generator 31 such as a piston for applying a force to the sample 22 and a sensor 32 for sensing a corresponding change of the sample 22 due to the applied force. Non-limiting embodiments of the sensor 32 include a strain sensor 33, a size measuring sensor 34 and an acoustic microphone or transducer 35. A processor 36 may process data received from the sensors to provide a rock deformation measurement.

Block 105 calls for measuring a rock deformation parameter of the sample using a sensor. The terms "deformation" or "damage" relate to physical changes to a rock that results from one or more forces applied to the rock. Non-limiting embodiments of the deformation parameter include a stress curve, a strain curve, and/or locations in the sample of stress and/or strain. Physical deformation such as strain may be measured with the strain sensor 33 coupled to the sample 22. External damage may be sensed by the size measuring sensor 34 configured to sense the size of the sample it undergoes an applied force. The internal damage of the plug may be monitored by measuring the acoustic emissions related to micro-cracking. That is, as a test force is imposed on the sample, the acoustic transducer 35 (or multiple transducers) receives acoustic energy (e.g., sound waves) related to the deformation or cracking of the sample. Using triangulation or other techniques, a location of a source of the acoustic energy (i.e., location of the deformation or cracking) can be determined. Also a repeated volumetric imaging and characterization run can provide supporting information on the degree and the distribution of internal damage. The data sets are to be used for verification purposes discussed in block 109 further below. The rock parameters obtained for the plug represent the bulk properties and are referred to hereafter as the physical "macro-properties".

Block 106 calls for constructing a mathematical model of the sample that replicates the determined internal rock damage and damage distribution of the sample. In one or more embodiments, the mathematical model is a digital three-dimensional model that is configured to be implemented by a processor such as in a computer processing system. In other embodiments, the model may have less than or greater than three dimensions. The model is also configured to model the evolution of micro-cracks and macro-cracks as the cracks develop due to applied forces. From the volumetric characterization of the plug, a digital representation is built for the purpose of a digital mechanical simulation. The representative, statistical and/or discrete distribution of matrix material, void space and damage (e.g. micro cracks) of the plug are represented in the digital model to replicate the plug's internal structure and damage. As noted above, one example of the digital model is a mechanism-based material model such as the modified Mohr-Coulomb model having a term representing dilatation in an out-of-plane orientation.

Block 107 calls for simulating the one or more tests using the mathematical model. The digital model is populated with plug's macro-properties derived from the physical tests carried out on the plug. The performed rock tests are simulated with the digital model of the plug using the mechanism-based material model capable of tracking the damage history and damage directionality. The parameters of the digital rock tests are collected. These may include the overall bulk characteristics of the test such as stress and/or strain curves and acoustic properties as well as discrete characteristics such as strain localization patterns, internal damage and/or acoustic emissions.

Block 108 calls for obtaining a rock deformation parameter using the one or more simulated tests corresponding to the measured rock deformation parameter.

Block 109 calls for comparing the rock deformation parameter obtained from the one or more simulated tests to the corresponding measured rock deformation parameter.

The results of the physical rock tests with bulk parameters and—upon availability—discrete observations (e.g. acoustic emissions, introduced physical damage as revealed by volumetric imaging etc.) are compared with the outcome of the digital simulation to determine if the outcome of the digital simulation matches the results of the one or more physical rock tests. The term "match" relates to determining if the outcome of the digital simulation is within a selected range, such as within 5% deviation for example, of the outcome of the physical rock tests. If several tests of the same type are performed, the range may be selected to provide a 95% confidence interval. The selected range in general will be determined by an amount of desired accuracy of the digital model.

Block 110 calls for adjusting one or more parameters of the mathematical model based upon the rock parameter obtained from simulation not being with a selected range of the measured rock parameter. If the bulk properties returned from the mathematical model simulation are different from those of the plug or if the discrete observations are different, then the mathematical model properties are adjusted. This will apply to the mathematical model's matrix properties, which are updated and the simulation is re-run until a match is achieved. The mathematical model can be calibrated with one or more parameters to predict material behavior that is consistent with experimentally observed material behavior. The parameters used to adjust the mathematical model are generally dependent on the specific mathematical model used. In the case of the modified Mohr-Coulomb model, such parameters include the initial damage parameter, initial values of fracture tensor components, and/or calibration coefficients for the relation between equivalent stress and strain rate, for grade dependence, for strain-rate dependence, and the like.

Block 111 calls for providing a latest mathematical model as a verified mathematical model based upon the rock deformation parameter obtained from simulation being with a selected range of the measured rock deformation parameter. That is, the latest iteration of the model for the latest run simulation that provides a match is designated as the verified mathematical model. In other words, the digital model can be called verified if the bulk properties and the bulk behavior are matching. It should be noted that blocks 106-111 are generally implemented using a processor.

The method 100 may also include performing an action on the earth formation using a parameter obtained from the verified mathematical model. For example, the verified mathematical model may be used to estimate rock strength parameters of a greater earth formation. Inserted as parameters in a subsurface geomechanical simulation, the rock strength parameters determine under which operational constraints the earth formation stays intact. From the estimated rock strength parameters inserted into the model those skilled in the art can optimize the development of hydrocarbon production by e.g. adjusting hydrocarbon pump rates, hereby avoid damage to the rock which may otherwise produce grains of sand. From the estimated intact rock strength combined with the in-situ stress the user can calculate the minimum bottom hole pressure for solid free production in a so-called sand production prediction analysis. The sand production prediction analysis uses rock mechanic calculations in combination with an experimental or empirical derived critical deformation parameter (such as a critical amount of strain) to calculate at which bottom hole pressure or reservoir pressure the wellbore wall will start to fail and grains will be transported in the produced fluids or gas. By controlling the production rates by changing valve settings at the well, the user can possibly avoid the solid production. In another example, the estimated rock strength parameter is used to determine a mud or drilling fluid weight that would avoid a collapse of a borehole being drilled. Based on the rock strength parameters of the earth formation, those skilled in the art will change the weight of the drilling fluid by adjusting its density to fall within safe operational limits. The weight limits being large enough to avoid the borehole collapsing upon itself due to the weight and stresses of the earth formation surpassing the limits of the rock strength. And the weight limits being small enough to avoid the formation of fractures as an effect of the drilling fluid pressure surpassing the rock strength parameters of the earth formation.

It can be appreciated that the method 100 providing the verified digital rock model has several advantages. One advantage is that the verified digital rock model has an accurate representation of the rock's micro- and macro properties which capture the effects of micro-cracks and damage. On the digital sample further forward modeling can be applied to run multiple simulated "destructive" tests with different configurations to obtain a more complete catalogue of rock properties. In contrast, a physical sample would only support a single destructive test from which limited information can be obtained (e.g. tensile strength, UCS). The possibility of repeated destructive tests allows one skilled in the art to obtain additional information, e.g. the rock strength as a function of confining pressure and/or of changes in temperature. This additional information helps to create a more complete model of material behavior, which is more useful for the application to subsurface conditions than limited information (e.g., no confining pressure at room temperature).

Another advantage is that the digital rock model can separate the matrix properties from the macro-properties. For example, the unconfined compressive strength (UCS) from samples without damage is expected to have higher values as opposed to the samples which have fractures. Under assumption of the matrix properties, a mechanism based material model can add any degree and distribution of damage to the sample to forward model the bulk rock properties of differently damaged rocks.

Next, examples of production equipment are discussed. FIG. 4 depicts aspects of production equipment for producing hydrocarbons from an earth formation. A production rig 40 is configured to perform actions related to the production of hydrocarbons from the borehole 2 (may also be referred to as a well or wellbore) penetrating the earth 3 having the earth formation 4. The formation 4 may contain a reservoir of hydrocarbons that are produced by the production rig 40. The production rig 40 may include a pump 41 configured to pump hydrocarbons entering the borehole 2 to the surface. The pump 41 may include a valve (not shown) for controlling the flow rate of hydrocarbons being pumped. The borehole 2 may be lined by a casing 45 to prevent the borehole 2 from collapsing. The production rig 40 may include a reservoir stimulation system 46 configured to stimulate the earth formation 4 to increase the flow of hydrocarbons. In one or more embodiments, the reservoir stimulation system 46 is configured to hydraulically fracture rock in the formation 4. The production rig 40 may also include a well rejuvenation system 47 configured to rejuvenate the borehole 2 (e.g., increase hydrocarbon flow into the borehole 2). In one or more embodiments, the well rejuvenation system 47 includes an acid treatment system configured to inject acid into the borehole 2.

The production rig 40 may also be configured to extract of core sample of the formation 4 a downhole coring tool 48. The downhole tool 48 may be conveyed through the borehole 2 by an armored wireline that also provides communications to the surface. The core sample may be extracted using an extendable core drill 49. Once the core sample is extracted, it is stored and conveyed to the surface for analysis. In general, a plurality of core samples is extracted in order to adequately represent the properties of rock present in the formation. For example, a higher number of samples would be required if the properties change significantly with depth as opposed to not changing significantly with depth.

FIG. 4 also illustrates a computer processing system 42. The computer processing system 42 is configured to implement the methods disclosed herein. Further, the computer processing system 42 may be configured to act as a controller for controlling operations of the production rig 40 to include core sample extraction and analysis. Non-limiting examples of control actions include turning equipment on or off, setting setpoints, controlling pumping and/or flow rates, and executing processes for formation stimulation and well rejuvenation. In general one or more of the control actions may be determined using a formation parameter obtained from the verified model. In one or more embodiments, the computer processing system 42 may update or receive an update of the verified model in real time and, thus, estimate the formation parameter and provide control actions in real time.

Figure 5:
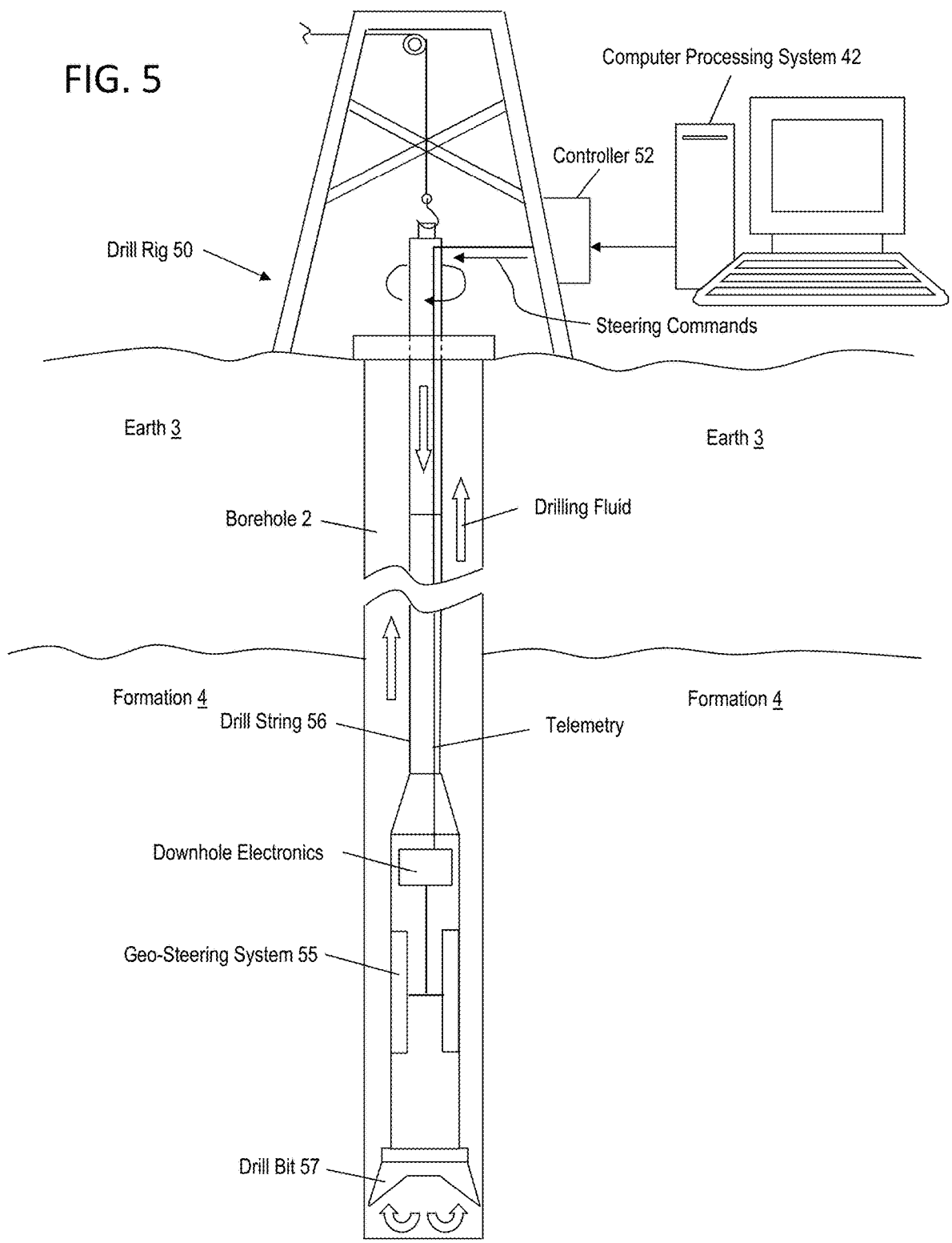
FIG. 5 depicts aspects of drilling equipment.

Next, examples of drilling equipment are discussed. FIG. 5 depicts aspects of drilling equipment. A drill rig 50 is configured to drill the borehole 2 into the earth 3 according to a desired trajectory or geometry. The drill rig 50 includes a drill string 56 and a drill bit 57 disposed at the distal end the drill string 56. The drill rig 50 is configured to rotate the drill string 56 and thus the drill bit 57 in order to drill the borehole 2. In addition, the drill rig 50 is configured to pump drilling mud (i.e., drill fluid) of a selected weight through the drill string 56 in order to lubricate the drill bit 57 and flush cuttings from the borehole 2. A geo-steering system 55 is coupled to the drill string 56 and is configured to steer the drill bit 57 in order to drill the borehole 2 according to the desired trajectory. A controller 52 is configured to control operations of the drill rig 50 to include controlling the geo-steering system 55. In one or more embodiments, the geo-steering system can control the direction of drilling by exerting a force on the borehole wall using extendable pads. The computer processing system 42 may provide inputs into the controller 52 based upon formation parameters estimated using the verified model. In one or more embodiments, the computer processing system may receive updates of the verified model in real time and, thus, estimate the formation parameter and provide inputs to the controller 52 in real time.

With respect to Block 106, discussed above, for constructing a mathematical model of the sample that replicates the determined internal rock damage and damage distribution of the sample, in one or more embodiments, the mathematical model is an artificial intelligence model, such as machine learning or deep learning model. Artificial intelligence (AI) refers to any kind of processor-executable set of instructions that have not entirely been provided in detail by a human, such as a programmer or software developer. In general, AI systems learn or identifiy model parameters based on data, fundamentally akin to a linear regression method that identifies slope and intercept of a line that represents a linear relationship between two parameters. Machine learning is one class of AI systems that encompasses—clustering, classification, regression and recommender systems. Deep learning systems utilize massive amounts of input data, oftentimes using neural networks with many layers, to model complex nonlinear relationships and to provide insight into data that more traditional methods are unable to reveal. It is noted that this disclosure includes any and all derivatives of neural networks, including convolutional neural networks, recursive neural networks, recurrent neutral network, and generative adversarial networks.

Constructing and applying a mathematical AI model includes two main phases: the training of a model such as an artificial neural network, and the consequent application of the model. A non-limiting example of individual steps of the workflow are summarized in FIG. 6.

Figure 6:
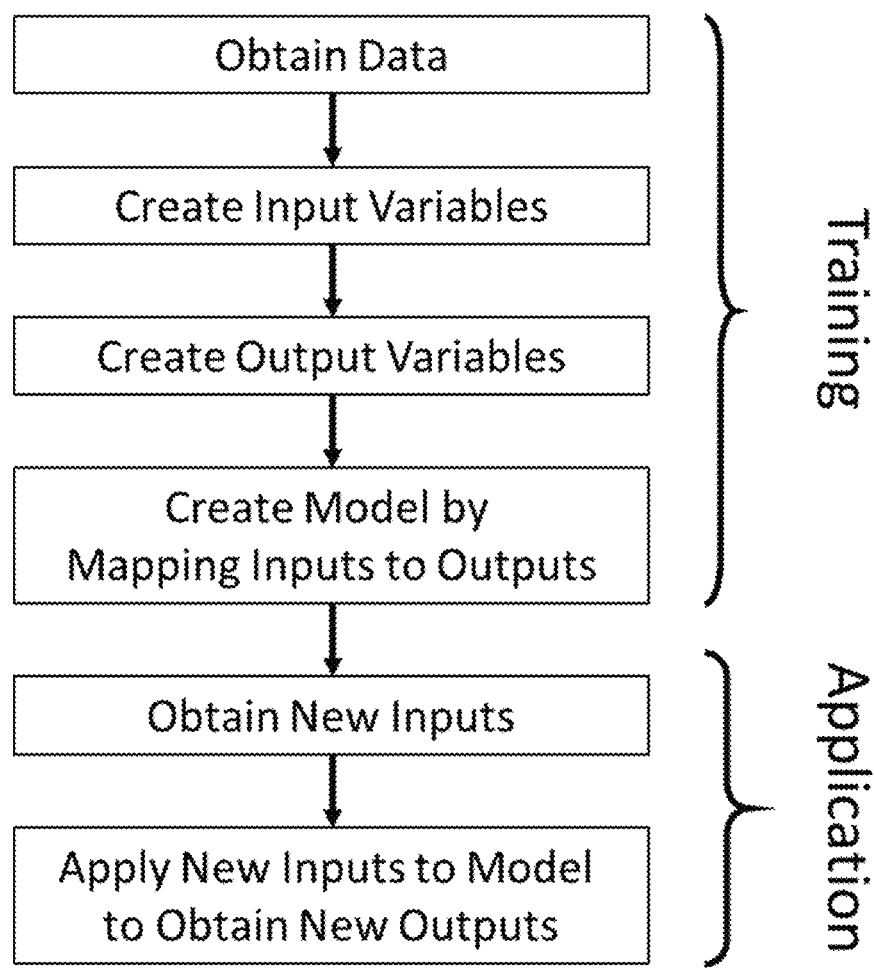
FIG. 6 depicts aspects of one example of workflow actions with respect to an artificial intelligence model of the sample.
Figure 7:
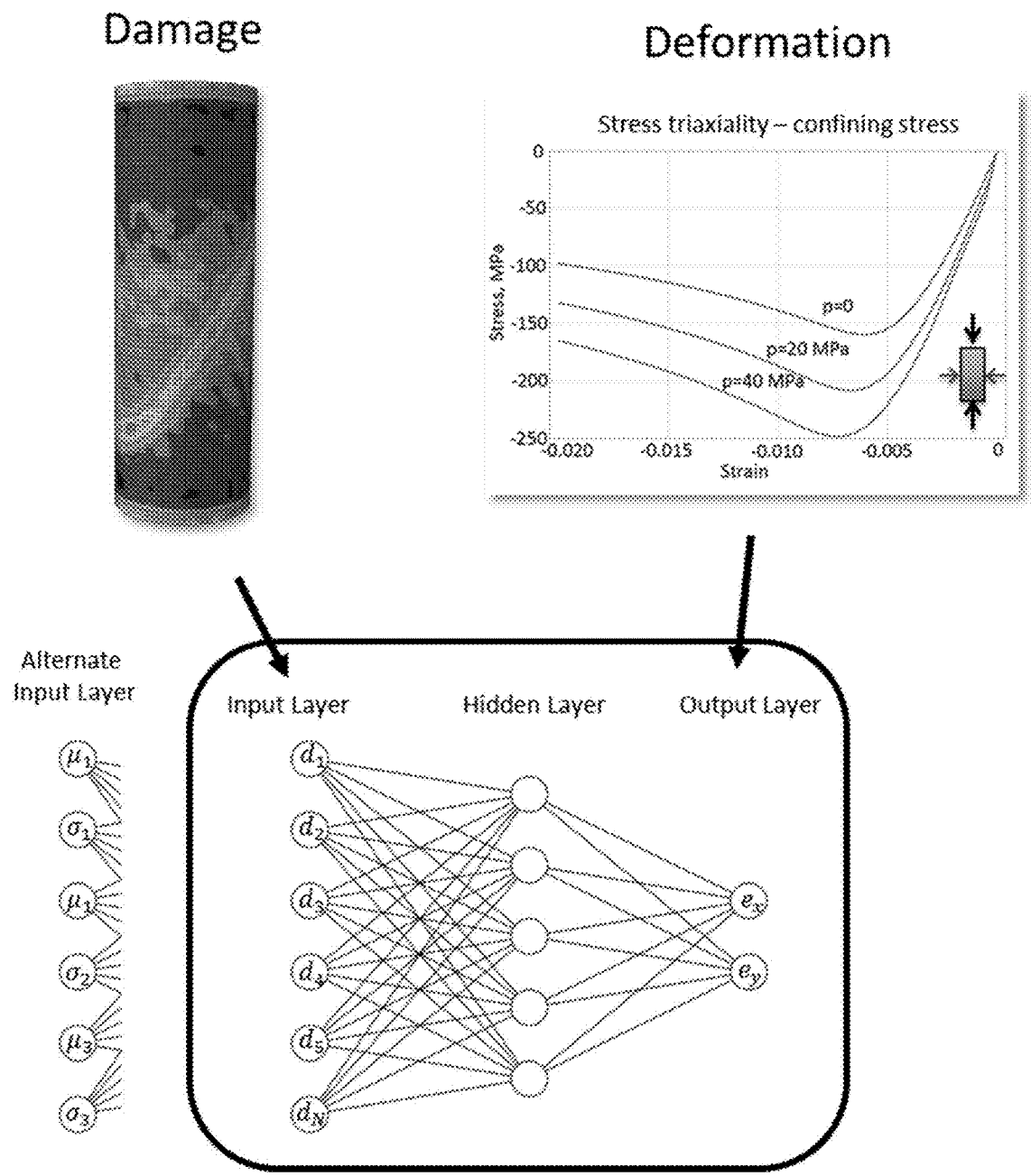
FIG. 7 depicts aspects of training an artificial neural network.

During the training phase illustrated in FIG. 6, a model is created that maps input variables to output variables. A good choice will be an artificial neural network, but other regression methods or multivariate statistics approaches can be substituted in place. An example of schematics of training a neural network is illustrated in FIG. 7. Specifically, FIG. 7 illustrates schematics of training an Artificial Neural Network to obtain deformation parameters. Inputs can be described as a vector of damage parameters, or as mean and standard deviation that describe different rock damage distributions, either in different rock sample partitions or on different length scales. Output parameters can be axial strain parameters or peak stress parameters in non-limiting embodiments.

In one embodiment, constructing a mathematical model of the sample that replicates the determined and measured internal rock damage and damage distribution of the sample includes creating a 3D volume map that describes damage values as a function of a coordinates in a coordinate system. An alternative to a 3D volume map can be a structured or unstructured grid, where data is defined on the grid cell centers, or the grid cell nodes, or the grid cell edges, or a combination thereof. Another alternative can be a structured or unstructured mesh of finite elements or finite volumes.

The input variables input into the machine learning or deep learning system can be a vector that consists of each these damage values, or it can be a vector that consists of values that are a function of these damage values. Such a function can be a local average, a minimum or maximum function, or a function that combines the damage with another parameter, e.g. fluid saturation, mineralogy or other parameters.

The input variables can also be of statistical nature. For instance, the damage values can be used to determine an underlying distribution, such as a normal distribution, a Weibull distribution, a power law distribution, a triangle or flat distribution or any other distribution. For instance, if the distribution of damage values is a normal (or Gaussian) distribution, it can be fully described by mean and standard deviation. Thus, two variables will be used to describe a rock sample's damage stage. If the distribution is of a different type, i.e. a power-law distribution, a similar approach can be used. If the distribution cannot typically be described by a certain distribution type (or combination thereof), a large-bin histogram can be used instead. In this case the number of input variables will increase quite substantially, but will still be smaller than using each 3D data point and will not present a conceptual or technical problem. In one embodiment, a distribution is defined for an entire rock sample. In another embodiment, more than one distribution is defined and two or more distributions are merged (e.g. added) with appropriate weights. In one embodiment, more than one distribution is used to represent different parts of the rock sample or different length scales of damage. In one embodiment, a distribution and damage are used together as input.

The output parameters can be deformation parameters of the sample. Deformation parameters can be axial strain in one or more particular direction, or volumetric strain, either measured directly or derived from axial strains. The strain measure can be taken at different points on stress-strain curves (see FIG. 7). For instance, the strain are peak stress, or the final strain, or the strain value where the response begins to deviate from linear behavior (e.g. using a threshold to pick the exact point of departure). Multiple strain values can also be used, for instance if the rock sample is imaged during the experiment and time-dependent mapping of rock damage (as imaged or derived from the imaging) and strain is obtained. Also, a combination of different stress values can be used, i.e. initial strain and strain at peak stress.

The output parameters may also be stress parameters. The stress measure can be taken at different points on stress-strain curves (see FIG. 7). For instance, the peak stress, or the final strain, or the stress value where the response begins to deviate from linear behavior (e.g. using a threshold to pick the exact point of departure). Multiple stress values can also be used, for instance, if the rock sample is imaged during the experiment and time-dependent mapping of rock damage (as imaged or derived from the imaging) and stress is obtained. Also, a combination of different stress values can be used, i.e. initial stress and peak stress. In this disclosure, the convention is used that negative stress values indicate compression and positive stress values indicate tension. Other conventions are possible without limiting the present invention.

In another embodiment, the input and output parameters can be switched, so that deformation parameters are used as input and rock damage as output parameters.

For the case of artificial neural networks, hyper-parameters such as the number of hidden layers, and the number of nodes in each hidden layer, can be optimized in a configuration or validation step that is part of training. Other AI methods can also be configured or tuned or optimized during validation steps. Optimization of the number of hidden layers and/or the number of nodes in each hidden layer may be based on the rock parameter obtained from simulation being maintained within the selected range of the measured rock parameter.

In machine learning applications, input vectors, which may be referred to as features, maybe normalized or sorted. This disclosure includes any data pipeline necessary for preparing the input data and output data. For instance, if the input data is a rock damage map, then the conversion from a volumetric rock damage description, which could be a list of tuples (x,y,z,d), where x,y,z are coordinates and d is the damage value, to a vector description d=(d1, d2, d3, d4, . . . ) might be part of the data pipeline.

During the application phase, either damage or deformation is given, and the mathematical model (machine learning, deep learning or similar) is used to obtain the corresponding other parameter, i.e., deformation or damage.

Set forth below are some embodiments of the foregoing disclosure:

Embodiment 1

A method for estimating a property of an earth formation, the method comprising: obtaining a sample of rock from the earth formation; scanning the sample with a volumetric imaging device to obtain a three-dimensional volume representation of the sample; determining internal rock damage of the sample using the three-dimensional volume representation of the sample; performing one or more tests on the sample using a rock test device; measuring a deformation parameter of the sample using a deformation sensor; constructing a mathematical model of the sample that replicates the determined and measured internal rock damage and damage distribution of the sample; simulating the one or more tests using the mathematical model; obtaining a rock deformation parameter using the one or more simulated tests corresponding to the measured rock deformation parameter; comparing the rock deformation parameter obtained from the one or more simulated tests to the corresponding measured rock deformation parameter; adjusting parameters of the mathematical model based upon the rock parameter obtained from simulation not being within a selected range of the measured rock parameter; and providing the mathematical model as a verified mathematical model based upon the rock parameter obtained from simulation being within a selected range of the measured rock parameter; wherein the determining, constructing, obtaining a rock deformation parameter, comparing adjusting, and providing are performed using a processor.

Embodiment 2

The method according to any prior embodiment, wherein obtaining a sample of rock comprises using a downhole coring tool.

Embodiment 3

The method according to any prior embodiment, wherein the testing comprises at least one of non-destructive testing and destructive testing.

Embodiment 4

The method according to any prior embodiment, wherein the destructive testing comprises multistage testing in which successive stages result in increasing damage.

Embodiment 5

The method according to any prior embodiment, wherein the deformation sensor comprises at least one of a strain sensor, a size measuring sensor, and an acoustic transducer.

Embodiment 6

The method according to any prior embodiment, wherein measuring comprises determining a location of damage using acoustic signals obtained from the acoustic transducer.

Embodiment 7

The method according to any prior embodiment, wherein the mathematical model comprises a modified Mohr-Coulomb model having a term representing dilatation in an out-of-plane orientation.

Embodiment 8

The method according to any prior embodiment, further comprising estimating a parameter of the earth formation using the verified mathematical model and performing an action related to the earth formation with action-related equipment using the estimated parameter.

Embodiment 9

The method according to any prior embodiment, wherein the parameter of the earth formation is unconfined compressive strength (UCS) of the earth formation and the action is pumping hydrocarbons from the earth formation using a pump at a flow rate determined by the unconfined compressive strength (UCS) in order to avoid sand grains from being pumped with the hydrocarbons.

Embodiment 10

The method according to any prior embodiment, wherein the parameter of the earth formation is unconfined compressive strength (UCS) and the action is pumping drilling fluid for drilling a borehole using drilling equipment, the drilling fluid having a weight that is selected using the unconfined compressive strength (UCS) that avoids collapse of the borehole.

Embodiment 11

The method according to any prior embodiment, wherein the mathematical model comprises a three-dimensional mathematical model.

Embodiment 12

A system for estimating a property of an earth formation, the system comprising: a volumetric imaging device configured to scan a sample of rock form the earth formation to obtain a three-dimensional volume representation of the sample; a rock test device configured to perform one or more tests on the sample; a deformation sensor configured to measure deformation of the sample due to the one or more tests; a memory having computer-readable instructions; a processor for executing the computer-readable instructions, the computer-readable instructions comprising: determining internal rock damage of the sample using the three-dimensional volume representation of the sample; constructing a mathematical model of the sample that replicates the determined internal rock damage and damage distribution of the sample; simulating the one or more tests using the mathematical model; obtaining a rock deformation parameter using the one or more simulated tests corresponding to the measured rock deformation parameter; comparing the rock deformation parameter obtained from the one or more simulated tests to the corresponding measured rock deformation parameter; adjusting parameters of the mathematical model based upon the rock parameter obtained from simulation not being with a selected range of the measured rock parameter; and providing the mathematical model as a verified mathematical model based upon the rock parameter obtained from simulation being within a selected range of the measured rock parameter.

Embodiment 13

The system according to any prior embodiment, further comprising a downhole coring tool configured to extract a sample of rock from the earth formation.

Embodiment 14

The system according to any prior embodiment, wherein the test equipment is configured to perform at least one of non-destructive testing and destructive testing.

Embodiment 15

The system according to any prior embodiment, wherein the deformation sensor comprises at least one of a strain sensor, a size measuring sensor, and an acoustic transducer.

Embodiment 16

The system according to any prior embodiment, wherein the computer readable instructions further comprise determining a location of damage using acoustic signals obtained from the acoustic transducer.

Embodiment 17

The system according to any prior embodiment, wherein the mathematical model comprises a modified Mohr-Coulomb model having a term representing dilatation in an out-of-plane orientation.

Embodiment 18

The system according to any prior embodiment, wherein the computer readable instructions further comprise estimating a parameter of the earth formation using the verified mathematical model and the system further comprises action-related equipment configured to perform an action using the estimated parameter of the earth formation.

Embodiment 19

The system according to any prior embodiment, wherein the parameter of the earth formation is unconfined compressive strength (UCS) of the earth formation and the action is pumping hydrocarbons from the earth formation using a pump at a flow rate determined by the unconfined compressive strength (UCS) that avoids sand grains from being pumped with the hydrocarbons.

Embodiment 20

The system according to any prior embodiment, wherein the parameter of the earth formation is unconfined compressive strength (UCS) and the action is pumping drilling fluid for drilling a borehole using drilling equipment, the drilling fluid having a weight that is selected using the unconfined compressive strength (UCS) that avoids collapse of the borehole.

Embodiment 21

A method for estimating a property of an earth formation, the method comprising: obtaining a sample of rock from the earth formation; scanning the sample with a volumetric imaging device to obtain a three-dimensional volume representation of the sample; determining internal rock damage of the sample using the three-dimensional volume representation of the sample; performing one or more tests on the sample using a rock test device; measuring a deformation parameter of the sample using a deformation sensor; constructing a mathematical model of the sample that replicates the determined and measured internal rock damage and damage distribution of the sample using artificial intelligence (AI), the mathematical model being an AI model; simulating the one or more tests using the mathematical model; obtaining a rock deformation parameter using the one or more simulated tests corresponding to the measured rock deformation parameter; comparing the rock deformation parameter obtained from the one or more simulated tests to the corresponding measured rock deformation parameter; adjusting parameters of the mathematical model based upon the rock parameter obtained from simulation not being within a selected range of the measured rock parameter; and providing the mathematical model as a verified mathematical model based upon the rock parameter obtained from simulation being within a selected range of the measured rock parameter; wherein the determining, constructing, obtaining a rock deformation parameter, comparing adjusting, and providing are performed using a processor.

Embodiment 22

The method according to any prior embodiment, wherein the constructing a mathematical model comprises performing a training phase to train the AI model.

Embodiment 23

The method according to any prior embodiment, wherein the training phase comprises: obtaining data related to the sample; creating input variables that are input into the AI model; creating one or more output variables that are output from the AI model; and creating the AI model by mapping the input variables to the one or more output variables.

Embodiment 24

The method according to any prior embodiment, wherein the input variables comprise a damage parameter that quantifies damage to the sample.

Embodiment 25

The method according to any prior embodiment, wherein the damage parameter comprises a statistical distribution of values of the damage parameter.

Embodiment 26

The method according to any prior embodiment, wherein the damage parameter is a function of position in the earth formation.

Embodiment 27

The method according to any prior embodiment, wherein at least one input variable is a function of a damage value.

Embodiment 28

The method according to any prior embodiment, wherein the function is one of local average, a minimum, a maximum, and a function that combines the damage value with another type of parameter.

Embodiment 29

The method according to any prior embodiment, wherein the another type of parameter comprises one of fluid saturation and mineralogy.

Embodiment 30

The method according to any prior embodiment, wherein the one or more output variables comprise a deformation parameter characterizing deformation of the sample.

Embodiment 31

The method according to any prior embodiment, wherein the deformation parameter comprises axial strain in one or more directions or volumetric strain.

Embodiment 32

The method according to any prior embodiment, wherein the one or more output variables comprise a stress parameter.

Embodiment 33

The method according to any prior embodiment, wherein the stress parameter comprises stress at a selected point on a stress-strain curve.

Embodiment 34

The method according to any prior embodiment, wherein the AI model comprises an artificial neural network and the training phase comprises optimizing hyper-parameters of the artificial neural network so that the rock parameter obtained from simulation is maintained within a selected range of the measured rock parameter.

Embodiment 35

The method according to any prior embodiment, wherein the simulating comprises performing an application phase to apply the AI model.

Embodiment 36

The method according to any prior embodiment, wherein the application phase comprises: obtaining new values of input variables; and applying the new values of input variables to the AI model to obtain new values of one or more output variables from the AI model.

Embodiment 37

A system for estimating a property of an earth formation, the system comprising: a volumetric imaging device configured to scan a sample of rock form the earth formation to obtain a three-dimensional volume representation of the sample; a rock test device configured to perform one or more tests on the sample; a deformation sensor configured to measure deformation of the sample due to the one or more tests; a memory having computer-readable instructions; a processor for executing the computer-readable instructions, the computer-readable instructions comprising: determining internal rock damage of the sample using the three-dimensional volume representation of the sample; constructing a mathematical model of the sample that replicates the determined internal rock damage and damage distribution of the sample using artificial intelligence (AI), the mathematical model being an AI model; simulating the one or more tests using the mathematical model; obtaining a rock deformation parameter using the one or more simulated tests corresponding to the measured rock deformation parameter; comparing the rock deformation parameter obtained from the one or more simulated tests to the corresponding measured rock deformation parameter; adjusting parameters of the mathematical model based upon the rock parameter obtained from simulation not being with a selected range of the measured rock parameter; and providing the mathematical model as a verified mathematical model based upon the rock parameter obtained from simulation being within a selected range of the measured rock parameter.

Embodiment 38

The system according to any prior embodiment, wherein the constructing a mathematical model comprises performing a training phase to train the AI model and the simulating comprises performing an application phase to apply the AI model.

Embodiment 39

The system according to any prior embodiment, wherein the AI model comprises damage values characterizing damage to the sample as a function of coordinates or as a function of defined grid cells imposed on the sample corresponding to where the damage values were obtained.

In support of the teachings herein, various analysis components may be used including a digital and/or an analog system. For example, the computer processing system 42, the controller 52, and/or the geo-steering system 55 may include digital and/or analog systems. The system may have components such as a processor, storage media, memory, input, output, communications link (wired, wireless, optical or other), user interfaces, software programs, signal processors (digital or analog) and other such components (such as resistors, capacitors, inductors and others) to provide for operation and analyses of the apparatus and methods disclosed herein in any of several manners well-appreciated in the art. It is considered that these teachings may be, but need not be, implemented in conjunction with a set of computer executable instructions stored on a non-transitory computer readable medium, including memory (ROMs, RAMs), optical (CD-ROMs), or magnetic (disks, hard drives), or any other type that when executed causes a computer to implement the method of the present invention. These instructions may provide for equipment operation, control, data collection and analysis and other functions deemed relevant by a system designer, owner, user or other such personnel, in addition to the functions described in this disclosure. Processed data such as a result of an implemented method may be transmitted as a signal via a processor output interface to a signal receiving device. The signal receiving device may be a display monitor or printer for presenting the result to a user. Alternatively or in addition, the signal receiving device may be memory or a storage medium. It can be appreciated that storing the result in memory or the storage medium will transform the memory or storage medium into a new state (containing the result) from a prior state (not containing the result). Further, an alert signal may be transmitted from the processor to a user interface if the result exceeds a threshold value.

Further, various other components may be included and called upon for providing for aspects of the teachings herein. For example, a sensor, transmitter, receiver, transceiver, antenna, controller, optical unit, electrical unit or electro-mechanical unit may be included in support of the various aspects discussed herein or in support of other functions beyond this disclosure.

Elements of the embodiments have been introduced with either the articles "a" or "an." The articles are intended to mean that there are one or more of the elements. The terms "including" and "having" are intended to be inclusive such that there may be additional elements other than the elements listed. The conjunction "or" when used with a list of at least two terms is intended to mean any term or combination of terms. The term "configured" relates one or more structural limitations of a device that are required for the device to perform the function or operation for which the device is configured.

The flow diagrams depicted herein are just examples. There may be many variations to these diagrams or the steps (or operations) described therein without departing from the spirit of the invention. For instance, the steps may be performed in a differing order, or steps may be added, deleted or modified. All of these variations are considered a part of the claimed invention.

The disclosure illustratively disclosed herein may be practiced in the absence of any element which is not specifically disclosed herein.

While one or more embodiments have been shown and described, modifications and substitutions may be made thereto without departing from the spirit and scope of the invention. Accordingly, it is to be understood that the present invention has been described by way of illustrations and not limitation.

It will be recognized that the various components or technologies may provide certain necessary or beneficial functionality or features. Accordingly, these functions and features as may be needed in support of the appended claims and variations thereof, are recognized as being inherently included as a part of the teachings herein and a part of the invention disclosed.

While the invention has been described with reference to exemplary embodiments, it will be understood that various changes may be made and equivalents may be substituted for elements thereof without departing from the scope of the invention. In addition, many modifications will be appreciated to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for estimating a property of an earth formation, the method comprising:
    obtaining a sample of rock from the earth formation;
    scanning the sample with a volumetric imaging device to obtain a three-dimensional volume representation of the sample;
    determining internal rock damage of the sample using the three-dimensional volume representation of the sample;
    performing one or more tests on the sample using a rock test device;
    measuring a deformation parameter of the sample using a deformation sensor;
    constructing a mathematical model of the sample that replicates the determined and measured internal rock damage and damage distribution of the sample using artificial intelligence (AI), the mathematical model being an AI model;
    simulating the one or more tests using the mathematical model;
    obtaining a rock deformation parameter using the one or more simulated tests corresponding to the measured rock deformation parameter;
    comparing the rock deformation parameter obtained from the one or more simulated tests to the corresponding measured rock deformation parameter;
    adjusting parameters of the mathematical model based upon the rock parameter obtained from simulation not being within a selected range of the measured rock parameter; and
    providing the mathematical model as a verified mathematical model based upon the rock parameter obtained from simulation being within a selected range of the measured rock parameter;
    wherein the determining, constructing, obtaining a rock deformation parameter, comparing adjusting, and providing are performed using a processor.

2. The method according to claim 1, wherein the constructing a mathematical model comprises performing a training phase to train the AI model.

3. The method according to claim 2, wherein the training phase comprises: obtaining data related to the sample; creating input variables that are input into the AI model; creating one or more output variables that are output from the AI model; and creating the AI model by mapping the input variables to the one or more output variables.

4. The method according to claim 3, wherein the input variables comprise a damage parameter that quantifies damage to the sample.

5. The method according to claim 4, wherein the damage parameter comprises a statistical distribution of values of the damage parameter.

6. The method according to claim 4, wherein the damage parameter is a function of position in the earth formation.

7. The method according to claim 3, wherein at least one input variable is a function of a damage value.

8. The method according to claim 7, wherein the function is one of local average, a minimum, a maximum, and a function that combines the damage value with another type of parameter.

9. The method according to claim 8, wherein the another type of parameter comprises one of fluid saturation and mineralogy.

10. The method according to claim 3, wherein the one or more output variables comprise a deformation parameter characterizing deformation of the sample.

11. The method according to claim 10, wherein the deformation parameter comprises axial strain in one or more directions or volumetric strain.

12. The method according to claim 3, wherein the one or more output variables comprise a stress parameter.

13. The method according to claim 12, wherein the stress parameter comprises stress at a selected point on a stress-strain curve.

14. The method according to claim 2, wherein the AI model comprises an artificial neural network and the training phase comprises optimizing hyper-parameters of the artificial neural network so that the rock parameter obtained from simulation is maintained within a selected range of the measured rock parameter.

15. The method according to claim 1, wherein the simulating comprises performing an application phase to apply the AI model.

16. The method according to claim 15, wherein the application phase comprises: obtaining new values of input variables; and applying the new values of input variables to the AI model to obtain new values of one or more output variables from the AI model.

17. A system for estimating a property of an earth formation, the system comprising:
a volumetric imaging device configured to scan a sample of rock form the earth formation to obtain a three-dimensional volume representation of the sample;
a rock test device configured to perform one or more tests on the sample;
a deformation sensor configured to measure deformation of the sample due to the one or more tests;
a memory having computer-readable instructions;
a processor for executing the computer-readable instructions, the computer-readable instructions comprising:
determining internal rock damage of the sample using the three-dimensional volume representation of the sample;
constructing a mathematical model of the sample that replicates the determined internal rock damage and damage distribution of the sample using artificial intelligence (AI), the mathematical model being an AI model;
simulating the one or more tests using the mathematical model;
obtaining a rock deformation parameter using the one or more simulated tests corresponding to the measured rock deformation parameter;
comparing the rock deformation parameter obtained from the one or more simulated tests to the corresponding measured rock deformation parameter;
adjusting parameters of the mathematical model based upon the rock parameter obtained from simulation not being with a selected range of the measured rock parameter; and
providing the mathematical model as a verified mathematical model based upon the rock parameter obtained from simulation being within a selected range of the measured rock parameter.

18. The system according to claim 17, wherein the constructing a mathematical model comprises performing a training phase to train the AI model and the simulating comprises performing an application phase to apply the AI model.

19. The system according to claim 17, wherein the AI model comprises damage values characterizing damage to the sample as a function of coordinates or as a function of defined grid cells imposed on the sample corresponding to where the damage values were obtained.

* * * * *